United States Patent [19]
Noiles et al.

[11] Patent Number: 5,358,533
[45] Date of Patent: Oct. 25, 1994

[54] SINTERED COATINGS FOR IMPLANTABLE PROSTHESES

[75] Inventors: Douglas G. Noiles, New Canaan; Alfred F. DeCarlo, Jr., Stamford, both of Conn.

[73] Assignee: Joint Medical Products Corporation, Stamford, Conn.

[21] Appl. No.: 7,059

[22] Filed: Jan. 21, 1993

Related U.S. Application Data

[62] Division of Ser. No. 838,577, Feb. 19, 1992, Pat. No. 5,263,986.

[51] Int. Cl.⁵ ............................ A61F 2/32; A61F 2/36; A61F 2/30
[52] U.S. Cl. .................................. 623/22; 623/23; 623/18
[58] Field of Search ................. 623/22, 23, 18, 16

[56] References Cited

U.S. PATENT DOCUMENTS

| | | |
|---|---|---|
| 3,605,123 | 9/1971 | Hahn . |
| 3,818,512 | 6/1974 | Shersher ............................ 623/22 |
| 4,156,943 | 6/1979 | Collier . |
| 4,206,516 | 6/1980 | Pillier . |
| 4,542,539 | 9/1985 | Rowe, Jr. et al. . |
| 4,629,464 | 12/1986 | Takata et al. . |
| 4,662,891 | 5/1987 | Noiles ............................... 623/22 |
| 4,713,076 | 12/1987 | Draenert . |
| 4,790,852 | 12/1988 | Noiles . |
| 4,813,965 | 3/1989 | Roberts . |
| 4,822,367 | 4/1989 | Stuhmer ............................ 623/22 |
| 5,021,063 | 6/1991 | Taber ............................ 623/22 X |
| 5,092,898 | 3/1992 | Bekki et al. ..................... 623/22 |
| 5,201,766 | 4/1993 | Georgette .................... 623/22 X |
| 5,211,665 | 5/1993 | Ku ................................... 623/22 |

FOREIGN PATENT DOCUMENTS

| | | |
|---|---|---|
| 2911754 | 10/1980 | Fed. Rep. of Germany . |
| 2590478 | 5/1987 | France ............................ 623/22 |
| 2651675 | 3/1991 | France ............................ 623/22 |

*Primary Examiner*—Randall L. Green
*Assistant Examiner*—Dinh X. Nguyen
*Attorney, Agent, or Firm*—Maurice M. Klee

[57] ABSTRACT

A sinterable coating for an implantable prosthesis is provided having 1) interstices into which tissue or bone can grow, and 2) increased surface roughness which provides enhanced initial press-fit fixation. The coating includes at least two sets of particles having different mean diameters. The sizes and numbers of particles are chosen so as to produce a matrix of smaller particles in which are embedded a lesser number of spaced-apart larger particles. The smaller particles provide support for the larger particles, and the larger particles stand proud of the smaller particles to provide the enhanced surface roughness.

4 Claims, 2 Drawing Sheets

SINTERED COATINGS FOR IMPLANTABLE PROSTHESES

This application is a divisional application of copending application Ser. No. 07/838,577 filed on Feb. 19, 1992, now U.S. Pat. No. 5,263,986.

BACKGROUND OF THE INVENTION

1. Field of the Invention

This invention relates to implantable prostheses and in particular to an improved sintered coating for such prostheses.

2. Description of the Prior Art

For at least the past twenty years, implantable prostheses have been coated with metal particles so as to provide a surface into which bone or tissue can grow. Such coatings have been applied by plasma spray and/or sintering. See, for example, Hahn, U.S. Pat. No. 3,605,123 and Pillier, U.S. Pat. No. 4,206,516. As a general rule, plasma spray coatings have a smaller void space than sintered coatings and thus are somewhat less preferred.

At present, a number of sintered coatings are in commercial use. The particles employed in these coatings are normally selected by sieving. They thus have a single-mode distribution about a mean diameter value. Typically, the mean value has been in the range from about 0.006 inches (150 microns) to about 0.040 inches (1000 microns), The breadth of the distribution about the mean will depend upon the sieves used to select the particles.

Sintered coatings of this type have been used in both single layer and multi-layer constructions, Also, they have been applied to prostheses having both smooth and stepped outer surfaces. See, for example, Noiles, U.S. Pat. No. 4,790,852.

One of the problems with the existing sintered coatings has been that relatively low levels of surface friction exist at the interface between the coating and the bone. Most prostheses are implanted by press fitting into a prepared cavity in the patient's bone. A high level of friction at the coating-bone interface is thus desirable because it helps provide a more stable initial fixation of the prosthesis in the prepared cavity. An initial stable fixation of the prosthesis has been found to increase the likelihood of bone ingrowth.

SUMMARY OF THE INVENTION

In view of the foregoing state of the art, it is an object of this invention to provide improved sintered coatings for implantable prostheses. More particularly, it is an object of the invention to provide sintered coatings which provide a high degree of surface friction at the coating-bone interface. It is a further object of the invention to provide improved coatings which can be readily manufactured using conventional techniques.

To achieve the foregoing and other objects, the invention provides a sintered coating having an irregular surface produced by the use of particles having at least a bimodal size distribution, as opposed to the single-mode size distribution used in the prior art. As used herein, the term "at least a bimodal size distribution" means that a plot of number of particles versus particle diameter has at least two discernible peaks. Such plots can be readily constructed using sieving techniques to construct a histogram or by simply counting and measuring particles for a representative portion of a coated prosthesis. In this connection, the diameter of a particle is defined as the longest chord between any two points on the surface of the particle.

The at least bimodal size distribution is preferably achieved by mixing together at least two sets of sieve-selected particles having different mean diameters. In general, it is preferred to select amounts of particles from the at least two sets so that the final distribution of particles includes more small particles than large particles. For example, for a coating made from two sets of sieve-selected particles, the ratio of the number of small particles to the number of large particles in the final distribution is preferably in the range from about 4 to about 40.

The at least bimodal particle mixture is applied to the prosthesis using the conventional techniques employed with single-mode particle distributions. Accordingly, the invention can be readily put into practice with essentially no changes to existing manufacturing techniques, which represents an important advantage of the invention.

In certain preferred embodiments, the particles are applied in substantially a single layer. In other preferred embodiments, the single layer is applied to a prosthesis having a stepped outer surface.

In practice, it has been found that prostheses coated with particles having size distributions of the type disclosed herein have significantly higher levels of surface friction in comparison to prostheses coated with similar particles having a single-mode distribution.

The accompanying drawings, which are incorporated in and constitute part of the specification, illustrate the preferred embodiments of the invention, and together with the description, serve to explain the principles of the invention. It is to be understood, of course, that both the drawings and the description are explanatory only and are not restrictive of the invention.

DESCRIPTION OF THE PREFERRED EMBODIMENTS

Figure 6:
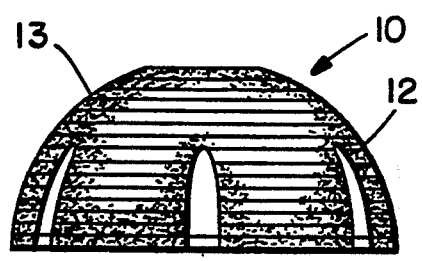
FIG. 6 shows an acetabular cup employing the coating of the invention.

As described above, the present invention relates to an improved sintered coating for implantable prostheses. The invention can be applied to all types of metal prostheses now known or subsequently developed, including, for example, hip and knee joint replacement prostheses. As an example, FIG. 6 shows an acetabular cup 10 having a body 12 and a coating 13 constructed in accordance with the invention.

The sintered metal coating is composed of a biocompatible metal, such as, pure titanium, a titanium alloy (e.g., Ti 6A1 4V; ASTM-F136), or a cobalt-chromium alloy (ASTM-F75). Typically, the metal coating will have the same composition as that of the underlying prosthesis.

The coating is applied to the prosthesis using conventional sintering techniques known in the art. The sintering is performed in a high temperature, vacuum furnace. The particles are applied to the prosthesis in a binder which is volatilized during the sintering process. Various companies provide coating services for metal prostheses which can be used in the practice of the invention, including Bio-Vac Inc. (Southfield, Mich.), Hy-Vac Technologies, Inc. (Detroit, Mich.), and Astro Met, Inc. (Cincinnati, Ohio).

In accordance with the invention, the surface of the coating is made irregular through the use of particles having at least a bimodal size distribution. Preferably, the bimodal size distribution is obtained by forming a mixture of at least two sets of sieve-selected particles having different mean diameters. The mixture is then used to coat the prosthesis.

The mean diameters for the at least two sets of particles and the numbers of particles from the sets are chosen so that 1) the final surface has spaced-apart larger particles embedded in a matrix of smaller particles, and 2) the larger particles stand proud of the smaller particles. The spaced-apart larger particles provide the desired roughness for the final surface. The smaller particles provide support for the larger particles so that the larger particles can resist the shear forces encountered during implantation and use of the prosthesis.

In contrast, if particles having a single-mode distribution were used to form a spaced-apart pattern having the same degree of roughness, the result would be a surface coating having many particles standing alone and therefore having only one point of integration with the prosthesis. Such isolated particles would have low shear strength and would be unsuitable for implantation in the body. The provision of a matrix of smaller particles solves this problem by providing numerous points of integration for each of the particles, i.e., both the smaller and the larger particles. The result is a strong, integrated coating having high shear strength. Moreover, the combination of at least two sets of particles produces a surface having numerous voids into which bone or tissue can grow.

Although the invention can be practiced with more than two sets of particles, for most applications a two set system will be adequate. To achieve 1) spaced-apart larger particles in a matrix of smaller particles and 2) larger particles standing proud of smaller particles, the larger particles for a two set system will generally have a mean diameter in the range of from about 2 to about 7 times the mean diameter of the smaller particles. Also, the number of smaller particles will be generally between about 4 and about 40 times the number of larger particles.

Furthermore, to insure that the larger particles stand proud of the smaller particles, the coating thickness should at most be a few layers and preferably should approach a single layer. Along these same lines, a stepped surface is preferred since the steps provide additional points of integration for the particles and contribute to the overall irregularity (roughness) of the final surface.

In practice, a mixture of equal measured volumes of 1) particles having a mean diameter of approximately 0.010 inches (250 microns), and 2) particles having a mean diameter of approximately 0.025 inches (630 microns), both determined by sieving, has been found to work successfully. For the particular particles used, the diameter range for the smaller particles was between about 0.007 inches (180 microns) and about 0.013 inches (330 microns), and the distribution for the larger particles was between about 0.017 inches (430 microns) and about 0.028 inches (710 microns).

In terms of particle numbers, if comparable packing configurations are assumed for the two sizes, the equal volumes correspond to a smaller particle to larger particle ratio of approximately 16:1. The use of particles of this type in a substantially single layer on a stepped surface has been found to result in a surface roughness substantially greater than that achieved with a single mode distribution of particles having a mean diameter anywhere in the range from about 0.010 inches (250 microns) to about 0.040 inches (1000 microns).

The differences between the particle distribution for the coatings of the invention and the particle distributions for prior art coatings is illustrated in FIGS. 1 through 5.

Figure 1A:
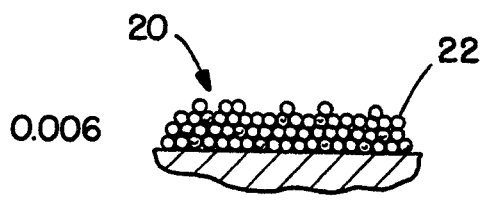
FIGS. 1A, 1B, and 1C are schematic diagrams illustrating typical constructions of prior art coatings.
Figure 1B:
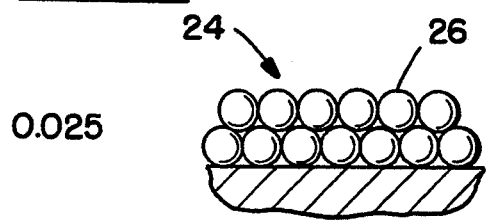
Figure 1C:
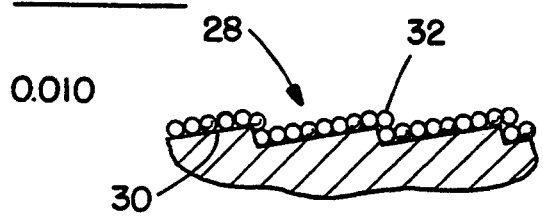

FIG. 1 shows cross-sectional views through typical coatings used in the prior art. More particularly, FIG. 1A shows a multi-layer construction 20 using relatively fine particles 22, e.g., particles having a mean diameter of about 0.006 inches (150 microns), FIG. 1B shows a multi-layer construction 24 using somewhat larger particles 26, e.g., particles having a mean diameter in the range from about 0.025 inches (630 microns) to about 0.040 inches (1000 microns), and FIG. 1C shows a single layer construction on a stepped prosthesis surface 30 using particles 32 having a mean diameter of about 0.010 inches (250 microns).

Figure 2A:
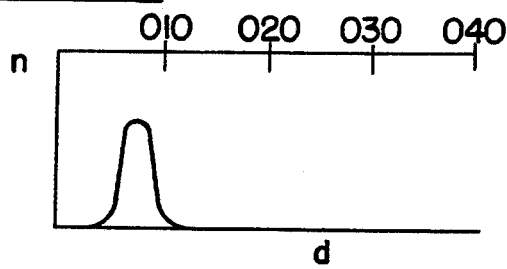
FIGS. 2A, 2B, and 2C show particle size distributions for the constructions of FIGS. 1A, 1B, and 1C, respectively.
Figure 2B:
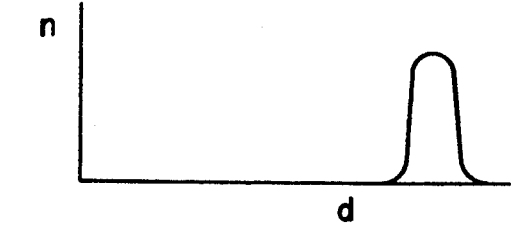
Figure 2C:
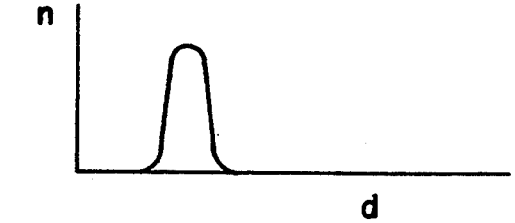

Representative plots of number of particles (n) versus particle diameter (d) for the constructions of FIGS. 1A, 1B, and 1C are shown in FIGS. 2A, 2B, and 2C, respectively. As shown therein, each of the distributions is single-moded, i.e., each distribution has one discernible peak.

Figure 3A:
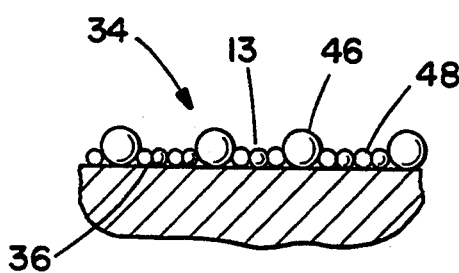
FIGS. 3A, 3B, and 3C are schematic diagrams illustrating representative constructions of coatings prepared in accordance with the invention.
Figure 3B:
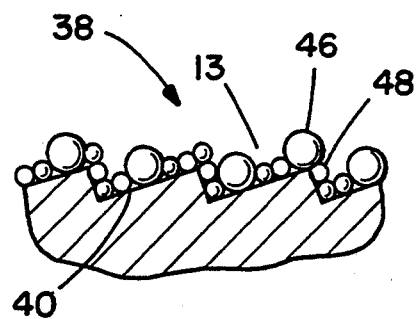
Figure 3C:
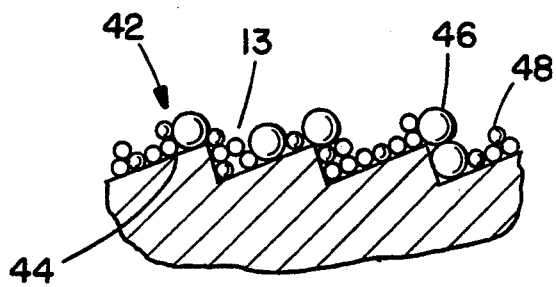
Figure 4:
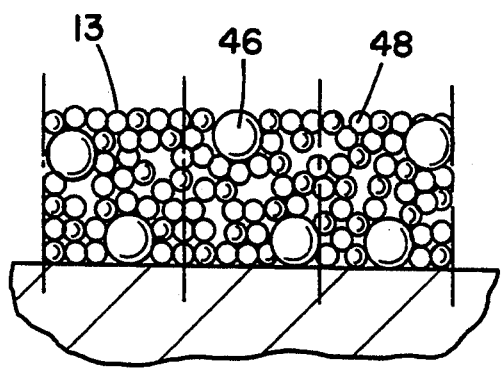
FIG. 4 is a plan view of the coatings of FIGS. 3B and 3C.

FIG. 3 shows cross-sectional views through representative coatings constructed in accordance with the invention using two sets of sieve-selected particles. In particular, FIG. 3A shows a single-layer construction 34 on a prosthesis having a smooth outer surface 36, FIG. 3B shows a single-layer construction 38 on a prosthesis having a stepped outer surface 40, and FIG. 3C shows a multi-layer construction 42 on a prosthesis having a stepped outer surface 44. FIG. 4 shows a plan view of the coating 13 for the constructions of FIGS. 3B and 3C. It should be noted in each of these figures that the distribution of the larger particles 46 within the matrix of the smaller particles 48 is substantially random.

Figure 5:
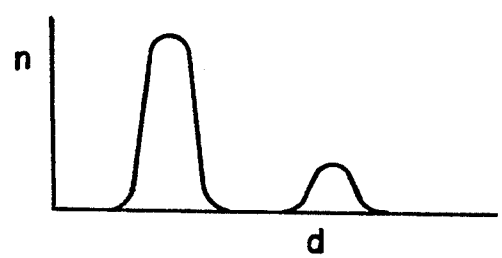
FIG. 5 shows the particle size distribution for the coatings of FIG. 3.

FIG. 5 is a plot of number of particles (n) versus particle diameter (d) for the constructions of FIG. 3. As shown in this figure, the distribution is bimodal, i.e., there are two discernible peaks in this figure. It should be noted that although the valley between the peaks in this figure drops to zero, in general, the distributions for the two sets can overlap so that the valley need not go all the way to zero. Also, if more than two sets of particle sizes are used, the n versus d plot will have more than two peaks.

Figure 7:
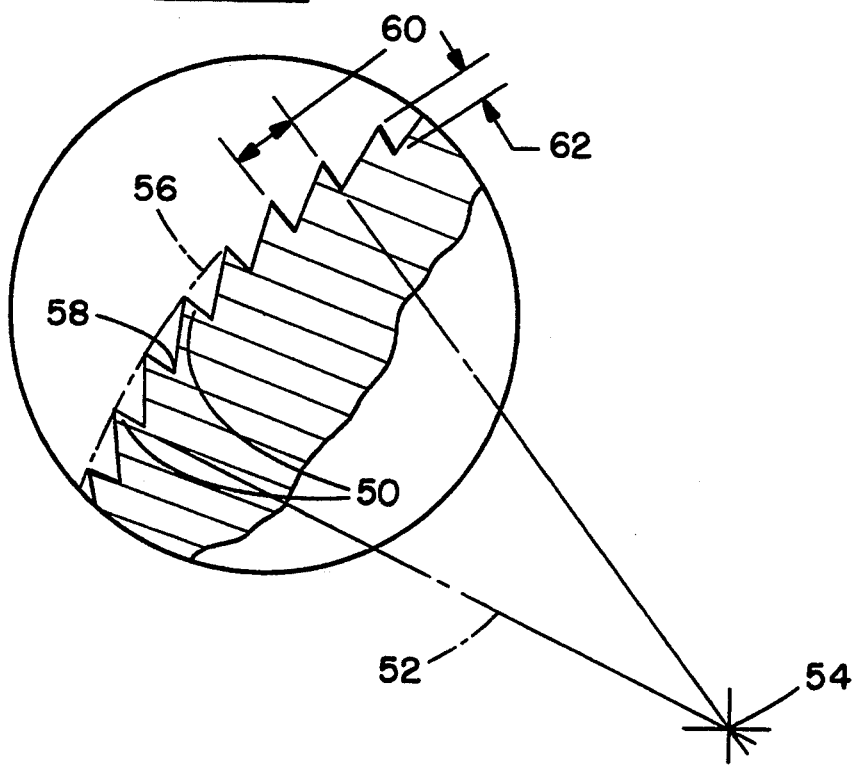
FIG. 7 is an expanded view of a portion of the surface of the acetabular cup of FIG. 6.

FIG. 7 shows a preferred construction for the stepped surface of FIG. 3C when used on a spherically-shaped cup of the type shown in FIG. 6. As illustrated in this figure, the cross-sectional shape of each step 50 is oriented similarly relative to a radial line 52 emanating from the center 54 of the sphere 56. This construction allows all of the steps to have a similar shape irrespective of their azimuthal location on the surface of the sphere. It also reinforces the adherence of the coating to the prosthesis when implanted in bone since the forces between the bone and the coating tend to drive the particles into the corners 58 of the steps. Preferably, the steps have azimuthal spacings 60 and radial depths 62 on the order of 2.5 millimeters or less and 1.0 millimeters or less, respectively.

A variety of modifications which do not depart from the scope and spirit of the invention will be evident to persons of ordinary skill in the art from the disclosure herein. The following claims are intended to cover the specific embodiments set forth herein as well as such modifications, variations, and equivalents.

What is claimed is:

1. An acetabular prosthesis for implantation in bone comprising a body having a substantially spherical outer surface at least a portion of which is stepped, said substantially spherical outer surface defining a pole, and said steps:

a) having similar radial cross-sectional shapes irrespective of their azimuthal locations on the surface of the prosthesis, and b) being substantially covered with a sintered coating of particles, each of said steps comprising a tread and a riser which intersect at a corner, said tread and riser being oriented so that the step opens towards the pole at said corner, whereby, when the prosthesis is implanted in bone, the forces between the bone and the sintered coating tend to drive the particles of the sintered coating into the corner.

2. The acetabular prosthesis of claim 1 wherein the azimuthal spacing between the steps is on the order of 2.5 millimeters or less.

3. The acetabular prosthesis of claim 1 wherein the radial depth of the steps is on the order of 1.0 millimeter or less.

4. The acetabular prosthesis of claim 1 wherein the sintered coating comprises at least two sets of particles having different mean diameters.

* * * * *

UNITED STATES PATENT AND TRADEMARK OFFICE
CERTIFICATE OF CORRECTION

PATENT NO. : 5,358,533
DATED : October 25, 1994
INVENTOR(S) : Douglas G. Noiles and Alfred F. DeCarlo, Jr.

It is certified that error appears in the above-identified patent and that said Letters Patent is hereby corrected as shown below:

Title page, item [62],   "Pat. No. 5,263,986" should read "abandoned"

Column 1, line 7,   "now U.S. Pat. No. 5,263,986" should read "now abandoned"

Signed and Sealed this

Sixth Day of June, 1995

Attest:

BRUCE LEHMAN

Attesting Officer    Commissioner of Patents and Trademarks